(12) United States Patent
Utz et al.

(10) Patent No.: US 11,852,884 B2
(45) Date of Patent: Dec. 26, 2023

(54) SYSTEMS AND METHODS FOR CONTROLLING MICROORGANISM LOAD WITH AN ELECTRONIC ILLUMINATOR

(71) Applicant: CHS HEALTHCARE VENTURES, INC, Decatur, GA (US)

(72) Inventors: Hans Utz, Decatur, GA (US); Dragan Nebrigic, Austin, TX (US)

(73) Assignee: CHS HEALTHCARE VENTURES, INC, Decatur, GA (US)

( * ) Notice: Subject to any disclaimer, the term of this patent is extended or adjusted under 35 U.S.C. 154(b) by 206 days.

(21) Appl. No.: 17/579,378

(22) Filed: Jan. 19, 2022

(65) Prior Publication Data

US 2022/0226564 A1 Jul. 21, 2022

Related U.S. Application Data

(60) Provisional application No. 63/138,961, filed on Jan. 19, 2021.

(51) Int. Cl.
*G02B 6/44* (2006.01)
*A61L 2/10* (2006.01)
(Continued)

(52) U.S. Cl.
CPC .............. *G02B 6/4482* (2013.01); *A61L 2/10* (2013.01); *A61M 5/14* (2013.01); *A61M 5/1582* (2013.01);
(Continued)

(58) Field of Classification Search
CPC .................... A61L 2/10; A61M 5/14–1418
See application file for complete search history.

(56) References Cited

U.S. PATENT DOCUMENTS

| 5,041,086 A | 8/1991 | Koenig et al. |
| 5,423,750 A | 8/1995 | Spiller |

(Continued)

FOREIGN PATENT DOCUMENTS

| AU | 2007282071 A1 | 2/2008 |
| CN | 102847204 A | 9/2012 |

(Continued)

*Primary Examiner* — Mariceli Santiago
(74) *Attorney, Agent, or Firm* — Bryan L. Baysinger; Maynard Nexsen PC

(57) ABSTRACT

Aspects of systems and methods for controlling SAR in medical infusion illumination are disclosed herein. In one aspect a system for reducing microorganism load in an environment surrounding an electronic illuminator is disclosed. In the system an electronic illuminator is disclosed comprising an LED module, a power driver equipped to the LED module for driving power to the LED, housing to protect the contents of the electronic illuminator and dissipate heat, and a PCB configured with an MCU for controlling operations within the electronic illuminator. Further, the system comprises a side emitting fiber optic line or line, also known as side glow fiber. The side emitting fiber optic line comprises a funnel cap for engaging with the electronic illuminator and a protective end cap for protecting and reflecting light radiation. In other aspects, a method for reducing microorganism count in an environment surrounding an electronic illuminator is disclosed. The method comprises provisioning an electronic illuminator equipped with an LED module and a side emitting fiber optic line. Then transmitting a signal, to a power driver of the LED module to begin the microorganism reduction. Next, emitting light radiation, by the LED module, and lastly terminating the light radiation after a set duration.

16 Claims, 13 Drawing Sheets

(51) Int. Cl.
*F21V 33/00* (2006.01)
*H05B 47/11* (2020.01)
*H05B 45/10* (2020.01)
*A61M 5/158* (2006.01)
*A61M 5/162* (2006.01)
*A61M 5/14* (2006.01)
*G16H 20/17* (2018.01)
*G16H 40/63* (2018.01)
*A61M 5/172* (2006.01)
*A61M 5/145* (2006.01)

(52) U.S. Cl.
CPC ............ *A61M 5/162* (2013.01); *A61M 5/172* (2013.01); *F21V 33/0068* (2013.01); *G02B 6/4442* (2013.01); *G16H 20/17* (2018.01); *G16H 40/63* (2018.01); *H05B 45/10* (2020.01); *H05B 47/11* (2020.01); *A61L 2202/14* (2013.01); *A61L 2202/24* (2013.01); *A61M 2005/1401* (2013.01); *A61M 2005/14553* (2013.01); *A61M 2205/14* (2013.01); *A61M 2205/3306* (2013.01); *A61M 2205/3313* (2013.01); *A61M 2205/3317* (2013.01); *A61M 2205/3633* (2013.01); *A61M 2205/587* (2013.01); *A61M 2205/6054* (2013.01); *A61M 2205/6081* (2013.01); *A61M 2205/8206* (2013.01); *A61M 2207/00* (2013.01); *F21V 2200/10* (2015.01)

(56) References Cited

U.S. PATENT DOCUMENTS

| | | |
|---|---|---|
| 5,681,285 A | 10/1997 | Ford et al. |
| 6,059,768 A | 5/2000 | Friedman |
| 7,860,583 B2 | 12/2010 | Condurso et al. |
| 8,679,075 B2 | 3/2014 | Lurvey et al. |
| 9,501,619 B2 | 11/2016 | Portnoy et al. |
| 10,232,107 B2 | 3/2019 | Utz |
| 2007/0106263 A1 | 5/2007 | Ward |
| 2010/0006171 A1 | 1/2010 | Tomlin et al. |
| 2011/0196306 A1 | 8/2011 | De La Huerga |
| 2011/0264463 A1 | 10/2011 | Kincaid et al. |
| 2013/0123579 A1 | 5/2013 | Adams et al. |
| 2013/0323119 A1* | 12/2013 | Alwan ...................... A61L 2/10 |
| | | 250/455.11 |
| 2016/0175521 A1 | 6/2016 | Adams et al. |
| 2017/0014023 A1 | 1/2017 | Kern |
| 2017/0021095 A1 | 1/2017 | Utz |
| 2017/0023216 A1 | 1/2017 | Utz |
| 2017/0258983 A1 | 9/2017 | Utz |
| 2017/0340815 A1 | 11/2017 | Utz |
| 2017/0281855 A1 | 12/2017 | Utz |
| 2018/0177938 A1 | 6/2018 | Provost et al. |
| 2019/0091398 A1 | 3/2019 | Utz |
| 2021/0338854 A1* | 11/2021 | Nissenbaum ............ A61B 1/07 |

FOREIGN PATENT DOCUMENTS

| | | | |
|---|---|---|---|
| EP | 1157711 A2 | 5/2008 | |
| EP | 2009533 A1 | 12/2008 | |
| WO | WO-2018100234 A1 * | 6/2018 | .......... A61L 2/0047 |
| WO | 2019164988 A1 | 8/2019 | |

* cited by examiner

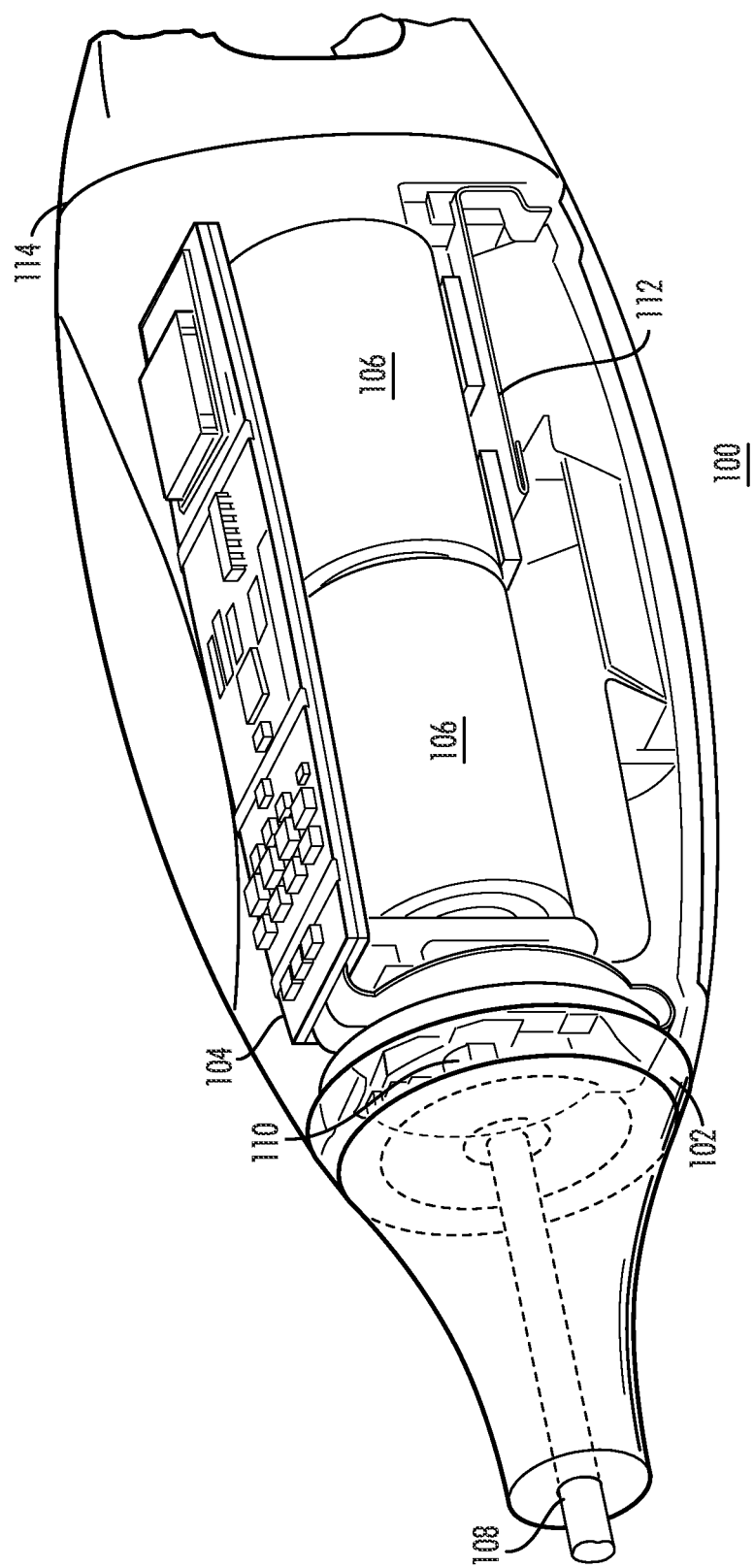

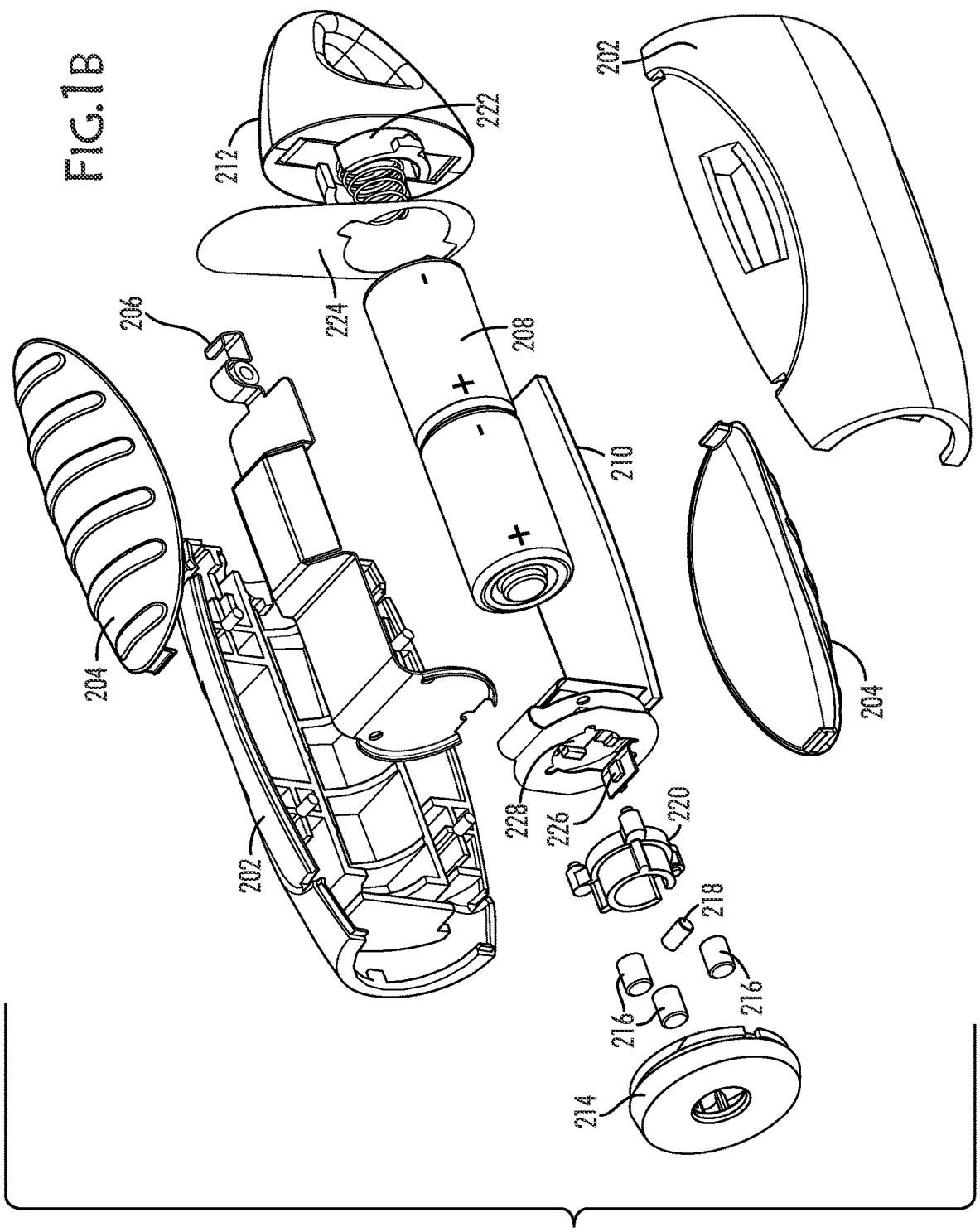

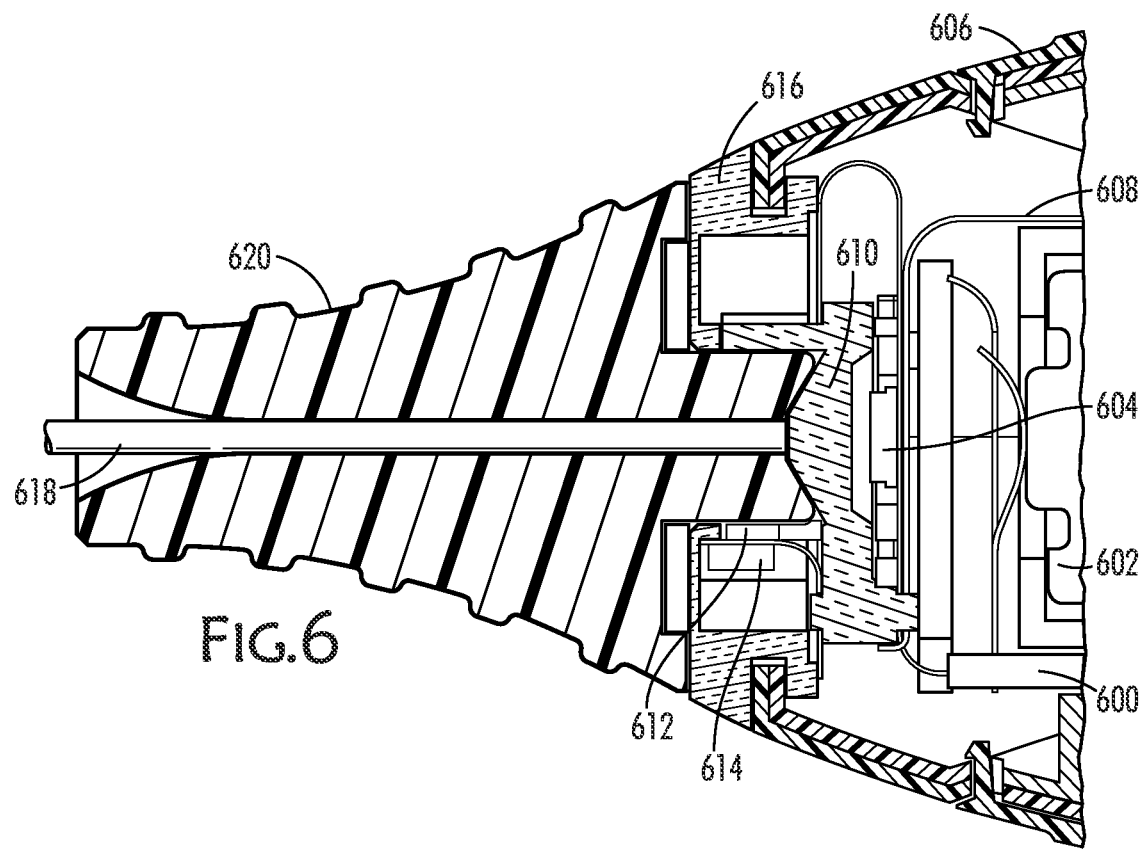
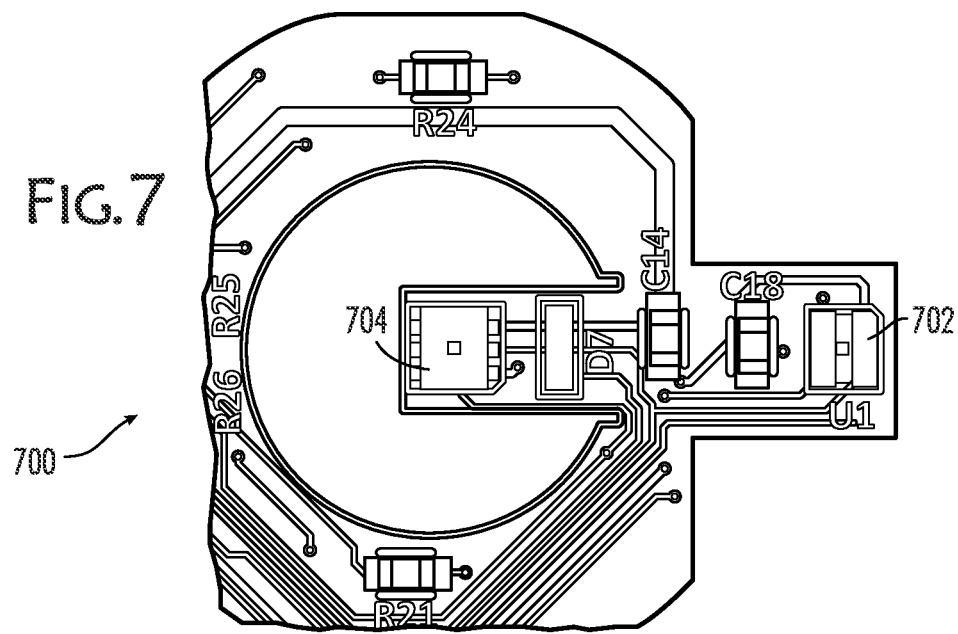

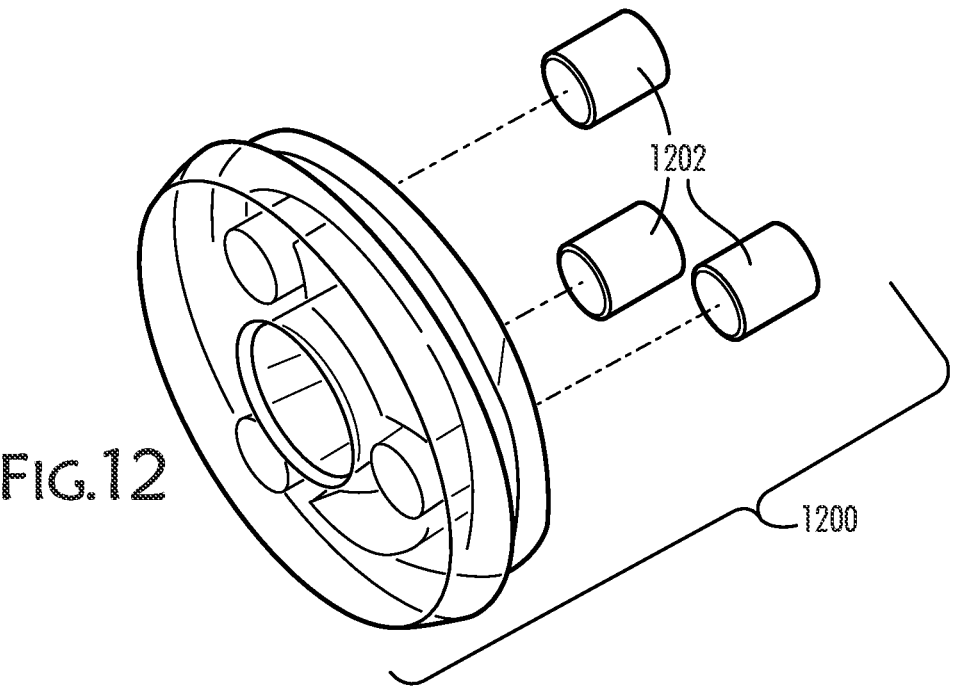
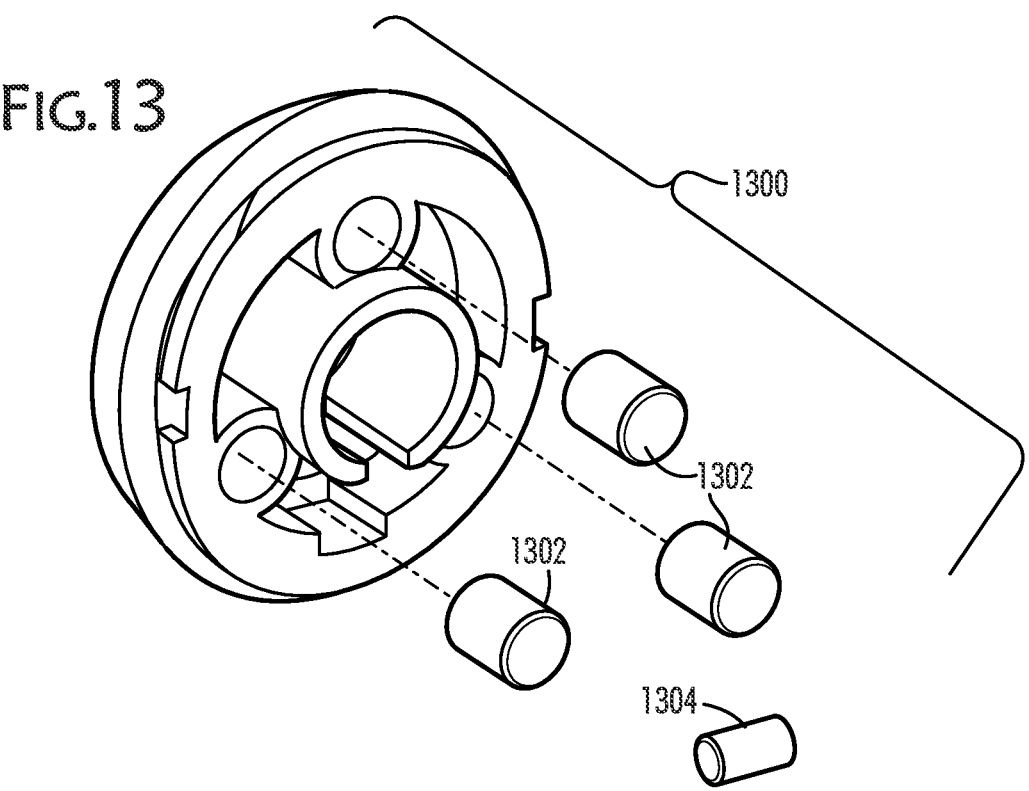

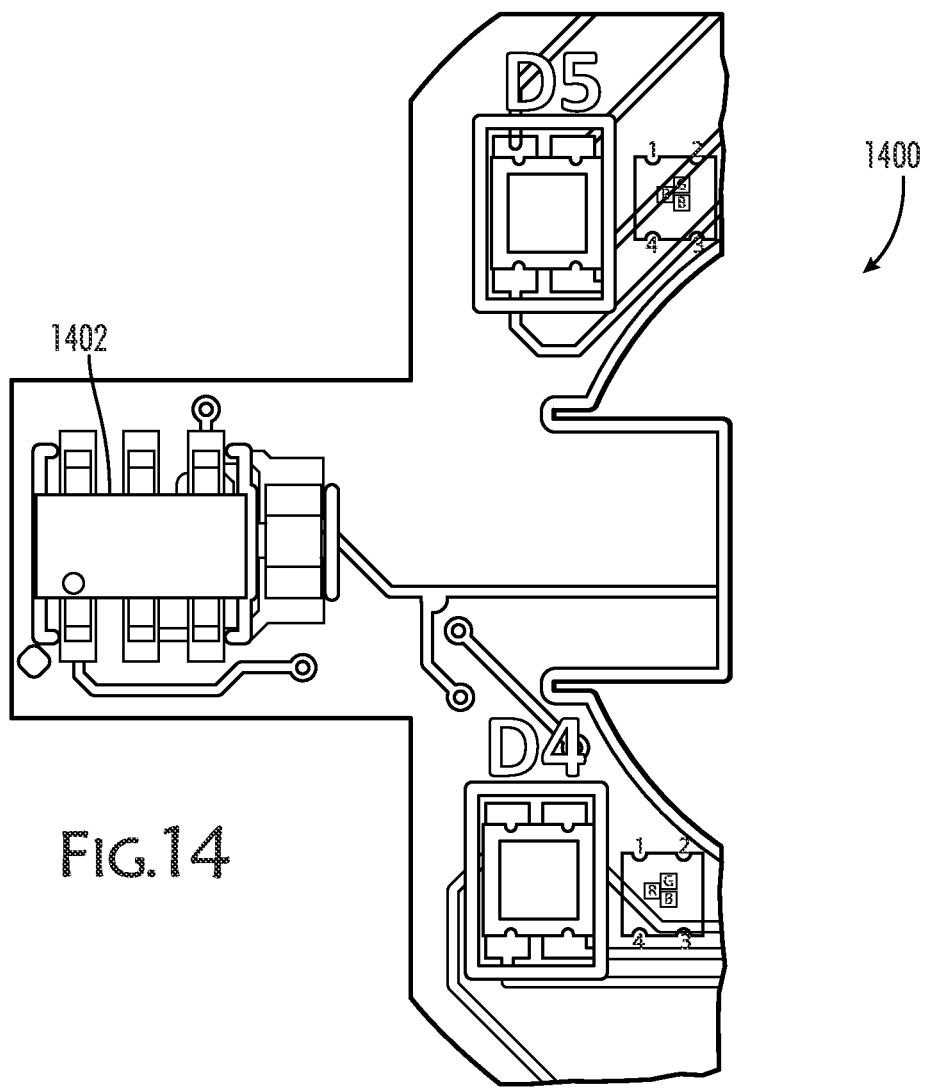

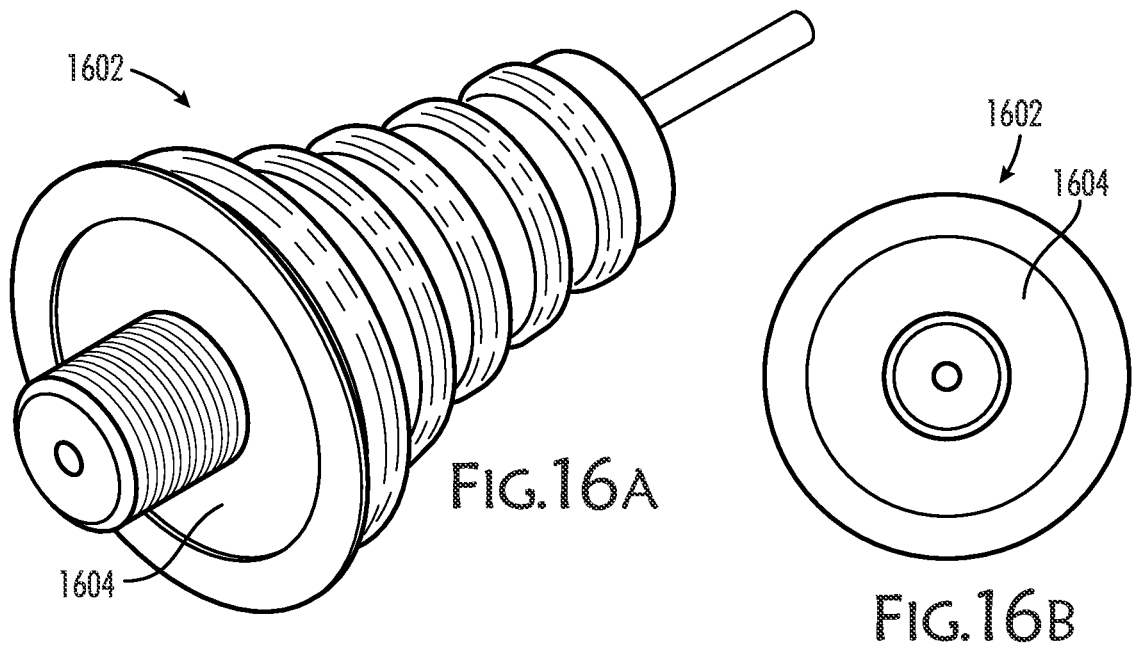
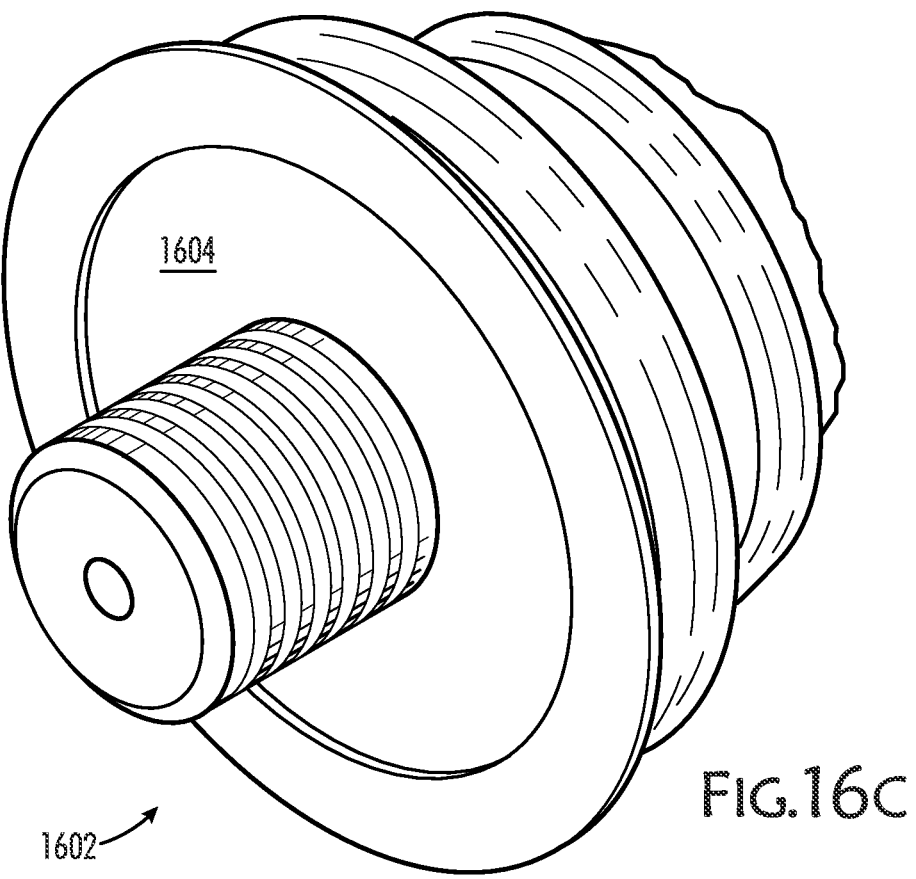

SYSTEMS AND METHODS FOR CONTROLLING MICROORGANISM LOAD WITH AN ELECTRONIC ILLUMINATOR

CROSS-REFERENCE TO RELATED APPLICATIONS

This application is related to and claims the priority of U.S. Provisional Patent Application No. 63/138,961 entitled "Electronic Illuminator" filed on Jan. 19, 2021. This application is also related to and co-filed with U.S. patent application Ser. No. 17/578,556, entitled "Assemblies and Subsystems for Electronic Illuminators"; and U.S. patent application Ser. No. 17/578,707, entitled "Medical Infusion Line Electronic Illuminator"; and U.S. patent application Ser. No. 17/589,206, entitled "Method and Manufacture of a Dual Lumen Fiber Optic Medical Infusion Line"; and U.S. patent application Ser. No. 17/578,761, entitled "Systems and Methods for Authenticating Medical Infusion Lines with an Electronic Illuminator." The entire disclosure of said applications are incorporated herein by reference.

FIELD

The present invention relates to controlling environmental microorganism load with electronic illumination of fiber optic lines. In particular, controlling microorganism load utilizing intelligence configured to an LED for microbial and viral load control of the system and environment.

BACKGROUND

The present disclosure relates generally to systems and methods for improving the administration of medical infusion utilizing light control and leveraging computational intelligence to advance patient care. Medical infusion typically serves to administer medications, fluids, nutrients, solutions, and other materials intravenously to a patient. Patients are often administered medical infusion using intravenous infusion tubes or lines ('IVT'). Such intravenous infusion tubes generally consist of flexible, polymer tubing connected at one end to a fluid source and at another end to a needle or port assembly that provides access to a blood vessel of a patient. The environment is often within a hospital or other care facility and may be surrounded by microbes and viral particles.

In 1903, Niels Ryberg Finsen won the Nobel Prize for discovering UV light could aid in the treatment of diseases. UV light is typically divided into three classes of wavelengths. The longest wave length is primarily UVA, ranging from 315 nm to 400 nm, UVA has limited bacterial and viral inhibiting potential and often requires microorganism to be subjected to such radiation for longer durations. Similarly, UVB, ranging from 280 nm to 315 nm also has limited bacterial and viral destroying potential, but requires shorter duration of use compared to UVA. Shorter wavelengths, such as UVC light or radiation, ranging from 100 nm to 280 nm, has the potential to damage or kill at least 99.9% of pathogenic microorganisms.

Optimization of UV radiation is one aspect of being able to kill a multitude of bacteria and virus microorganisms. The most common germicidal light or radiation is 254 nm, which is often produced by low pressure mercury lamps. Similarly, intense pulsed light ('IPL') may be used along the same lines of UV radiation, wherein short duration pulses may prove harmful to microorganisms, thus altering their ability to survive in the environment.

Thus, the problem addressed by the disclosure herein is a system and method for reducing microorganism load on an illuminating infusion line, as well as reducing microorganism load in the surrounding environment. Therefore, the disclosure herein allows for illuminated medical infusion as well as reducing environmental microbial and viral contaminants. Thus improving patient outcomes and increasing reusability of the systems disclosed herein.

SUMMARY

Aspects of the systems and methods herein utilize computing technology, including microcontrollers, and integrated circuits to perform tasks associated with improving the usage of medical infusion tubes. Aspects of systems and methods for controlling SAR in medical infusion illumination are disclosed herein. In one aspect a system for reducing microorganism load in an environment surrounding an electronic illuminator is disclosed. In the system an electronic illuminator is disclosed comprising an LED module, a power driver equipped to the LED module for driving power to the LED, housing to protect the contents of the electronic illuminator and dissipate heat, and a PCB configured with an MCU for controlling operations within the electronic illuminator. Further, the system comprises a side emitting fiber optic line or line, also known as side glow fiber that is capable of emitting a complete spectrum, including UV and visible light. The side emitting fiber optic line comprises a fiber funnel cap for engaging with the electronic illuminator and a protective end cap for protecting and reflecting light radiation.

In another aspect, a method for reducing microorganism count in an environment surrounding an electronic illuminator is disclosed. In said aspect, the method begins by provisioning an electronic illuminator equipped with an LED module and a side emitting fiber optic line. The electronic illuminator may be one with a housing or may be configured or integrated within a medical infusion pump. Next, transmitting a signal, by a MCU on a PCB of the electronic illuminator, to a power driver of the LED module. Then, emitting light radiation, by the LED module, within a range of 100 nm to 400 nm. Lastly, terminating the light radiation, by a second signal from the MCU to the power driver of the LED module. The method may further emit light radiation from a UVC LED module. The module may be incorporated as part of the existing LED module or may be configured to the flexible region of the PCB to form an additional LED element. Further, the method is configured to reduce microorganism count by utilization of UV spectrum for adequate duration, emitting along the length of the side scattering fiber optic line.

BRIEF DESCRIPTION OF THE DRAWINGS

Many aspects of the present disclosure will be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views. It should be recognized that these implementations and embodiments are merely illustrative of the principles of the present disclosure. Therefore, in the drawings:

FIG. 1A is perspective view of an illustration of an example electronic illuminator, displaying the configuration of internal components and subsystems;

FIG. 1B is an exploded view of an illustration of an example electronic illuminator;

FIG. 6 is an illustration of an example of an electronic illuminator in cross section, disclosing the ambient light sensor configuration within the electronic illuminator;

FIG. 7 is an illustration of an example of an electronic illuminator's Rigid-Flex PCB, wherein the flex portion is disclosed with the ambient light sensor and the cap color detection assembly;

FIG. 12 is an illustration of an example cap and magnet assembly for an electronic illuminator, the configuration provides aspects of the fiber detection assembly;

FIG. 13 is an additional illustration of an example cap and magnet array with a steel bar for an electronic illuminator, the configuration provides aspects of the fiber detection assembly;

FIG. 14 is an illustration of an example fiber detection assembly, wherein the Rigid-Flex PCB is disclosed with a hall effect sensor;

FIGS. 16A-C are illustrations of a fiber funnel cap that is configured to a side scattering fiber optic line, and is configured to engage with an electronic illuminator.

DETAILED DESCRIPTION

Figure 2:
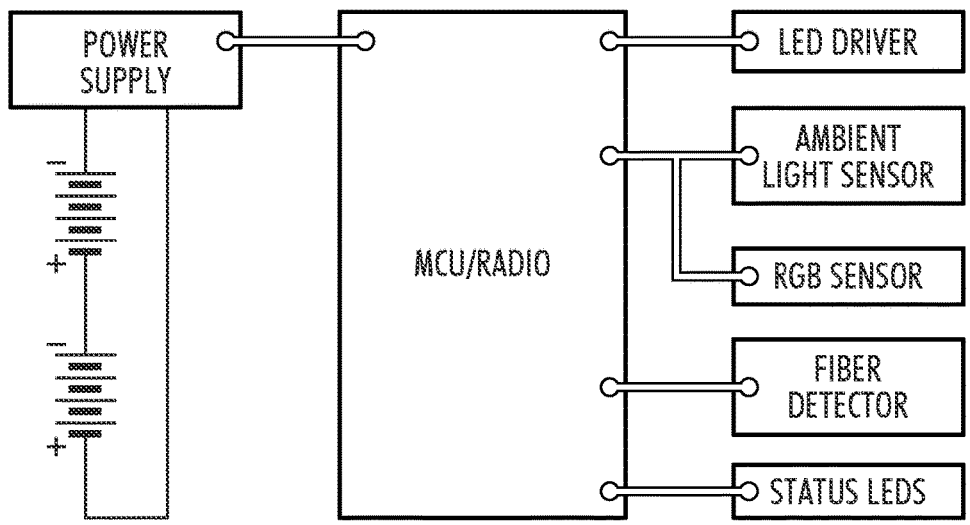
FIG. 2 is a schematic diagram of an example of an electronic illuminator's internal components and subsystems.

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Throughout this specification and the claims, the terms "comprise," "comprises," and "comprising" are used in a non-exclusive sense, except where the context requires otherwise. Likewise, the term "includes" and its grammatical variants are intended to be non-limiting, such that recitation of items in a list is not to the exclusion of other like items that can be substituted or added to the listed items.

I. Example Use Case Scenarios

Medical infusion occurs within medical environments or facilities where healthcare workers and patients are numerous. In such facilities and environments, microorganism load or count is a constant concern. Modern facilities include many air quality measures, such as air filters and chemical means. However, few medical devices are designed to be self-cleaning, in on aspect, the disclosure herein provides for reducing microorganism load by UV spectrum within the environment of the system. In other aspects, a routine is scheduled for "self-cleaning" so that microorganism load remains under control. In additional aspects, the systems herein may be utilized as routine microorganism control, adding to an automated system within medical environments.

In other aspects, a fluid transmission channel and a light transmission channel are combined to form an illuminated medical infusion line. Wherein the fiber optic cable is fed through the light transmission channel, and fluids and medicines travel along the fluid transmission channel. In one aspect the light transmission channel, comprising the fiber optic cable configured to the electronic illuminator, transmit UV light or radiation along the entire length of the light transmission channel, conducting a "cleaning" routine wherein microorganism load is reduced due to the UV radiation.

II. Systems and Methods

In one aspect, the LED is configured to the electronic illuminator and is controlled through a printed circuit board ('PCB'). In the example the PCB is a Rigid-Flex PCB ('RF-PCB') (herein also referred to generally as a 'PCB') wherein part of the board is rigid and the other part is defined within a flexible ribbon, thus allowing for applications such as within the electronic illuminator housing or a medical infusion pump. The electronic illuminator is configured to illuminate a side scattering fiber optic line having a proximal end with a fiber funnel cap and a terminal end that terminates in a protective cap. The fiber optic may be side glow or fuzzy fiber optic line, also known as side scattering or side emitting fiber optic line, that allows light to emanate or leak to the outside, causing a glow or luminescence.

In one aspect environmental microbial and viral control is achieved by transmitting ultraviolet light (UV), a form of electromagnetic radiation with a wavelength from 10 to 400 nm. Short wave UV light alters or damages DNA of microbes and viruses and cleans surfaces with which it comes into contact with. In the example embodiment of the electronic illuminator, the LED power driver is capable of driving short, medium, and long wave UV light from an LED, and therefore providing an anti-microbial routine for the electronic illuminator. Typical UV-LED's range from 365-395 nm wavelengths, but additional UV-LEDs are available to cover shorter spectrum in the UVB and UVC range. Further, in other aspects a UV laser is equipped and configured to the electronic illuminator and is controlled by the microcontroller. Similar to the UV-LED, the UV laser is capable of transmitting UV spectrum through the side emitting fiber optic line along the entire length, therefore providing anti-microbial support for the system and environment. In even further embodiments IR spectrum is utilized for anti-microbial purposes, similar to the disclosure of UV spectrum. In additional aspects, a diode or sensor may be equipped to an onboard MCU to assist in adjusting and setting parameters around the UV spectrum transmitted, including such items as power, duration, and scheduling.

Hospitals and health care centers have special requirements for sanitization as they are continually impacted by patients with a variety of diseases, as well as requirements for lowering microbial load. In one aspect the system provides anti-microbial support in the network and within surrounding systems and apparatus through emitting UV radiation that inhibits or hinders bacterial growth or virus particles. In additional aspects intense pulsed light ('IPL') is used, from the power driver in the electronic illuminator a IPL integrated system is equipped for anti-microbial support and maintenance. IPL is non-thermal and allows the use of light to reduce the microbial load, while not interfering with the applications and instruments in the surrounding environment.

In an additional aspect, the electronic illuminator is sealed to prevent ingress and egress of moisture, microorganisms, and other contaminants. In another aspect the sealed environment houses a plurality of UV spectrum generating fixtures. Including the capability to generate UVA/UVB/UVC. Additional UV aspects may be available, such as FUV, MUV, NUV, EUV, and VUV. It will be known by those of skill in the art the benefits of applying UV radiation for reducing the microbial load and maintaining the systems and apparatuses involved. Further, the modular aspects and applications of applying a variety of spectrum allows the electronic illuminator to serve a variety of purposes, including utilization as an anti-microbial beam or anti-microbial device or apparatus.

Specific absorption rate or SAR is a measure of the rate at which energy is absorbed per unit mass by a human body when exposed to radiation, such as UV radiation. SAR measures exposure to fields between 100 kHz and 10 GHz, and in the medical field is most often associated with radiation from MRI scans. The value of SAR depends heavily on the part of the body exposed, along with the location and geometry of the radiation source.

Lastly, certain medicines require specific light frequency to activate. This field is often referred to as photo pharmacology, and utilizes light to switch molecules for targeted therapies within the body. The disclosure herein provides for the side scattering fiber optic line to emit light radiation at specific frequencies to activate medicines. Such medicines may be controlled through precise radiation levels, and durations by the electronic illuminator. For example, certain cancer medicines may be activated by illumination as they travel along a fluid transmission channel in a medical infusion line.

III. With Reference to Figures

Referring now to FIG. 1A, a perspective view of an illustration of an example electronic illuminator, displaying internal components and subsystems. In the example, an electronic illuminator 100 is disclosed with a fiber funnel cap that may also be referred to as a funnel cap. The fiber funnel cap, in the example, may be of a specific color, wherein when inserted into the receiving unit of the electronic illuminator 100, the color is detected and the electronic illuminator 100 is set to illuminate the LED driver corresponding to cap color. This feature reduces cognitive load as it is intuitive, wherein a red cap will configure the electronic illuminator 100, through an MCU, to display a red light down the fiber optic line 108. In this example, the fiber optic line 108 being a side emitting or side scattering fiber optic line, or one with poor transmission that allows light filter outside of the directionality of the line.

Continuing, in the example, a RF-PCB 104 is disclosed, wherein the flex portion is folded unto itself, forming a location for the R/G/B sensor of a cap color detection system. The folds allow for blocking of the ambient light sensor from the onboard LED of the electronic illuminator, wherein the ambient light sensor acquires environmental lux from the clear housing, also referred to as a translucent ring 102, at the proximal end of the electronic illuminator 100. In other aspects the translucent ring 102 may be opaque or may have a window in it that allows for environmental light. In further embodiments the light from the side emitting fiber optic line may be used to determine environmental lux. Additionally, the magnets supplied for the hall effect sensor forming the fiber detection assembly are embedded within the translucent ring 102, or positioned near the translucent ring 102, to form a magnetic field.

A battery 106 is disclosed along with an internal heat sink 112, wherein the battery powers the electronic illuminator's various assemblies and the internal heat sink 112 works to dissipate heat to the external heat sink on the housing. In one aspect the battery 106 is a lithium chemistry battery. In the example, an LED assembly 110 is positioned to connect with the fiber funnel cap to project light along the side emitting fiber optic line 108. An end cap 114 to the electronic illuminator holds the batteries in place and may further house a communications module or assembly as well as an antenna. The communications module may be a radio frequency communications module such as 3G, 4G, 5G, and LTE.

The electronic illuminator, in one aspect, may work in coordination with the ambient light sensor and the cap color detection assembly or the fiber detection assembly to regulate usage of power and to form a swarm of sensors for intelligent power management and battery control. In one aspect, the ambient light sensor detects lux in the environment and controls LED power output from the power driver to conserve energy. Further, the cap color detection assembly may detect the fiber funnel cap is not engaged and thus automatically turn the system off. Similarly, the fiber detection assembly may detect an absence of a fiber and a fiber funnel cap, therefore turning the power off until the fiber funnel cap is attached.

The electronic illuminator, in one aspect, comprises a housing, along with a rigid-flex PCB or RF-PCB or PCB, and a power source. The housing may be comprised of a polymeric material and have various metal or other heat transferring locations, effectively forming external heat sinks within the housing that connects to an internal heat sink. Further, in other aspects, the housing may be comprised of metal or a blend of polymeric material and a metal, thus forming a protective enclosure for the various assemblies and subsystems. In one aspect the housing allows the electronic illuminator to be water tight or dust proof, and in other aspects it may be rated for waterproofing for a certain period of time at specific atmospheric pressure. Rubber gaskets may align the surfaces of the housing, as well as rubber material for grip, such as textured rubber where a user may come into contact with the electronic illuminators housing. The rubber gaskets assist in water proofing, vibration, dust proofing, and may further attribute to ingress protection, allowing some examples to achieve ratings such as IP65, IP66, and IP67.

Returning to the RF-PCB, in one example it may be configured with an ambient light sensor that is operatively configured within the housing of the electronic illuminator. The ambient light sensor may be any number of makes or models, for example, it may be a sensor manufactured by Lite-On™, such as the LTR-329ALS-01. In one aspect, the flexible region of the RF-PCB allows for adjusting and aligning the ambient light sensor to offset from the LED, therefore allowing for detection of whether or not the LED is powered, along with the LED's relative intensity, and detection of environmental lux. These features incorporated with the onboard microcontroller allow for automatic light intensity configuration through the power drivers on the RF-PCB. In another aspect the ambient light sensor converts light intensity to a digital signal, such as lux, thought an analog to digital converter on the sensor, and transmits the lux value to a microcontroller. In another aspect the conversion is processed on a microcontroller on the RF-PCB, and further used to determine behavior of an electronic illuminator. Even further embodiments, the processing may occur on a microprocessor, wherein the microprocessor may be standalone, or it may be incorporated onto the microcontroller unit.

Referring now to additional aspects of the electronic illuminator. In one aspect the housing may be further comprised of a heat sink. The heat sink may be metal based or based from other transferable materials that allow the dissipation of heat energy from the LED, the power drivers, the microcontroller, and the various microprocessors onboard an example system. Furthermore, the heat sink may be aligned with the power source, such as a battery. The battery may comprise any number of chemistries that are available to provide durational power support for the electronic illuminator.

Referring now to FIG. 1B, an exploded view of an illustration of an example electronic illuminator. In the example a housing 202 has locations for an external heat sink 204, wherein the external heat sink 204 is in thermal connection with an internal heat sink 206. The internal heat sink 206 is designed to contact equipment such as the LED power drivers, the LED, and other integrated circuits or microcontrollers, including processing units, so as to reduce heat build-up and control thermals within the tight enclosure. The housing of the example electronic illuminator is further configured with an end cap 212, the end cap having a negative terminal 222. The end cap 212 secures the batteries in place and allows for rapid exchange of batteries. In the example, the end cap 212 has split paper 224 to separate the contact of the batteries and allow for an extended shelf life of the electronic illuminator. Additionally, a translucent ring 214 forms the proximal end or end nearest the fiber optic line, wherein the translucent ring 214 allows light to reach an ambient light sensor Similarly, in additional embodiments a window to the environment may be provided, wherein the translucent ring is opaque or not translucent and a window within the ring may allow for observing the lux within the environment.

Various examples disclosed herein contain reference to the electronic illuminator, and are identified in FIG. 1B. In one aspect the illuminator is housed within a front shell and a back shell, also referred to as a housing 202. The housing is often made of a polymer but can be made of other materials such as a metal casing. The housing of the electronic illuminator serves to protect the assemblies, sensors, and controllers, as well as provide positioning of said components, and account for size, durability, and ease of transmission of RF signals. An electronic illuminator end cap 212 secures a lithium ion or other battery 208 in place within the shell or housing 202 of the electronic illuminator. The end cap 212 is equipped to receive a piece of split paper 224 to break the current and allow for longer shelf life and storage of the electronic illuminator. In additional aspects an internal heat sink 206, which is integrated along the PCB 210 and/or microcontroller and battery supply or batteries 208, the internal heat sink 206 is then connected through a high thermal conductive material to the metal side covers, or external heat sinks 204 to further dissipate heat. In other aspects the metal side cover is fully formed to the internals of the electronic illuminator and provides a passive environmental cooling complex.

In another aspect of the example of FIG. 1B, power is supplied from a plurality of batteries 208, which may be of lithium chemistry, or other chemistry, to allow for powering an electronic illuminator. Additionally, the electronic illuminator's batteries 208 may be charged wirelessly or through a uniform serial bus connection such as a USB-B, USB-C, or any micro variants thereof. The RF-PCB 210, also known herein as a PCB, contains a microcontroller, along with the various assemblies and sensors. The RF-PCB 210 forms a folded structure to allow for unique positioning of sensors and assemblies so as to allow for optimal operation. In one aspect, the ambient light sensor is formed to the backside of the RF-PCB 210, so that ambient light from the environment, penetrating through the translucent ring 214 is the only perceived light. This allows for automatic adjustment by the MCU for controlling light intensity. For example, if the surrounding environment is dark, the amount of lux produced by the LED can be lower, as the overall system needs do not require a high lux operation, thus conserving battery life and equipment from excess heat and usage.

The LED assembly 228 on the RF-PCB 210 is configured with a lens 220, wherein the lens 220 is situated to receive the fiber for illumination. The fiber side, in one aspect, is equipped with a fiber funnel cap, that configures to the translucent ring 214 and is held in place by a locking mechanism or through magnetic force and use of magnets 216. The R/G/B sensor 226, comprising the cap color detection assembly, is disclosed facing inwards toward the receiving orifice of the fiber funnel cap. Additionally, the magnet assembly 216, in coordination with the steel bar 218 provides a magnetic flux key or signature that may be utilized for fiber detection, as well as authentication and security. Wherein the electronic illuminator may be configured to authorize use of a signature or flux key.

Referring now to FIG. 2, a schematic diagram of an example of an electronic illuminator's internal components and subsystems. In one aspect a microcontroller unit or MCU is configured to a power supply such as a battery or may be directly powered through a USB connection to a power source external to the device. Similarly, the power supply may be adapted to receiving power wirelessly through such standards as Qi charging. The schematic of FIG. 2 is an overall generalization of an example of an electronic illuminator, including components such as an LED driver, ambient light sensor R/G/B sensor (which forms a cap color detection assembly), a fiber detection assembly (based in part on a hall sensor), status LED's, and a power supply.

The various components, assemblies, sensors, and subsystems may be in communication utilizing an inter-integrated circuit ('I²C') interface for intra-board communication. Additional communications protocols such as wireless, Bluetooth™, and other radio standards may be additional chipsets configured with the onboard MCU.

Figure 3:
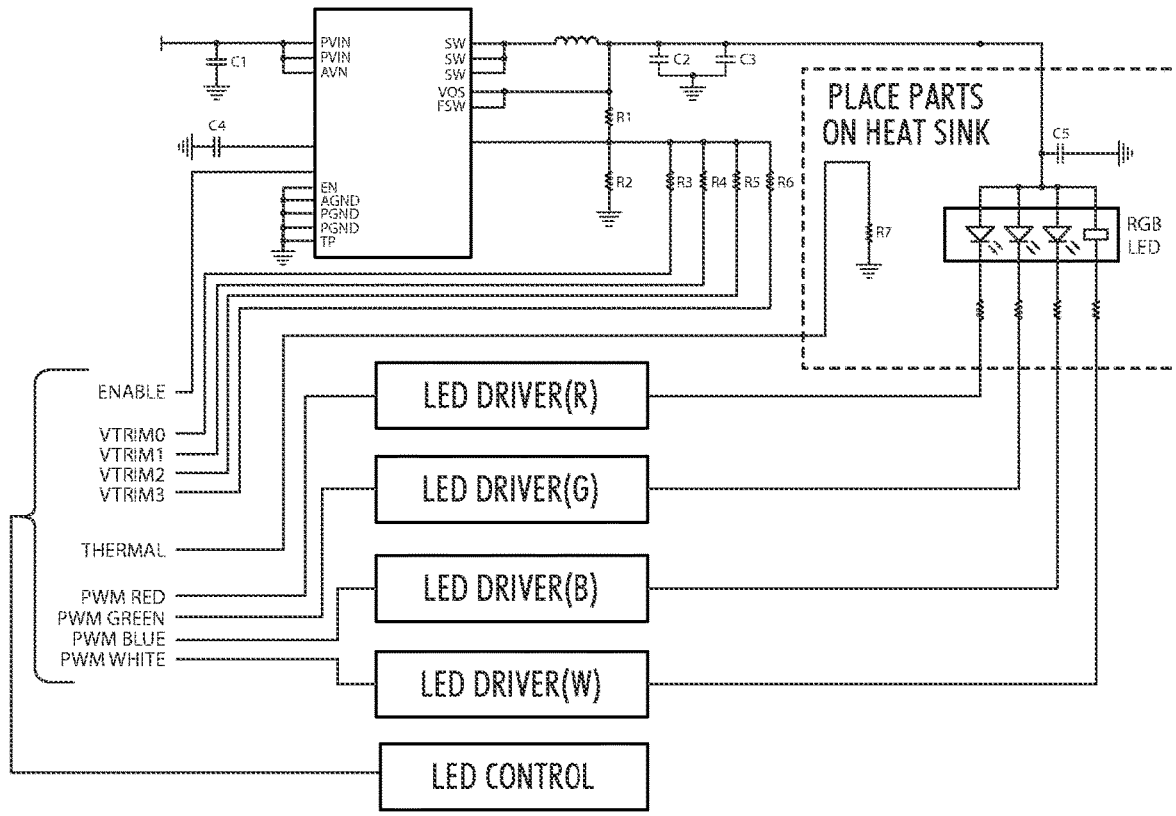
FIG. 3 is a schematic diagram of an example of an electronic illuminator's LED power system drivers.

Turning now to FIG. 3, a schematic diagram of an example of an electronic illuminator's LED power system drivers. In one aspect the power drivers illuminate LED's for varying color frequency. In the disclosed example, a red, green, blue, and white driver powers the various aspects of color. Due to heat or radiance or thermals from the drivers powering the LED components, a heat sink may be applied, such as the one disclosed in FIG. 1B, wherein the heat is diffused along an electronic illuminator, and dispersed exterior thereof through a heat sink mounted externally. Thus, the present embodiment is an internal metallic heat sink in thermal communication with an external facing metallic heat sink. Additional configurations of the LED drivers, as well as LED powering assembly and the chipset are disclosed herein.

Figure 4:
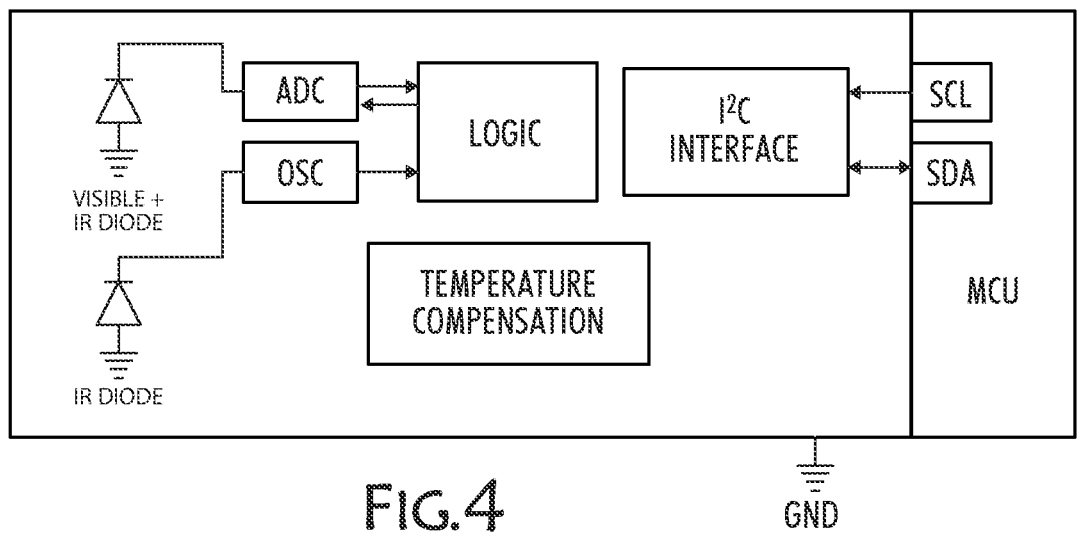
FIG. 4 is a block diagram of an example of an electronic illuminator's ambient light sensor.

Referring now to FIG. 4, a block diagram of an example of an electronic illuminator's ambient light sensor. In one example the ambient light sensor converts light intensity to a digital output signal capable of direct inter-integrated circuit—I²C. With reference to FIG. 4, the Analog to Digital Converter ('ADC'), is configured to the visible IR diode and IR diode, wherein the logic is responsible for converting. Continuing, in the example, the I²C interface is displayed in connection with the Serial Clock ('SLC') and serial data. Thereby, I²C being a synchronous, multi-controller, multi-target, packet switched, single-ended serial communications bus. I²C uses only two bidirectional open collector or open drain lines, serial data line and serial clock line, pulled up with resistors. Typical voltages used are +5 V or +3.3 V, although other voltages are common.

In the example of FIG. 4, within operating temperatures within a range of 30° Celsius to 70° Celsius, the example ambient light sensor may perceive 6 dynamic ranges from 0.01 lux to 64,000 lux, and automatically reject 50/60 Hz lightings flicker. Thus, in the example surface mount package, the ambient sensor converts light intensity to a digital output signal that is capable of direct I²C interface with an MCU.

Figure 5:
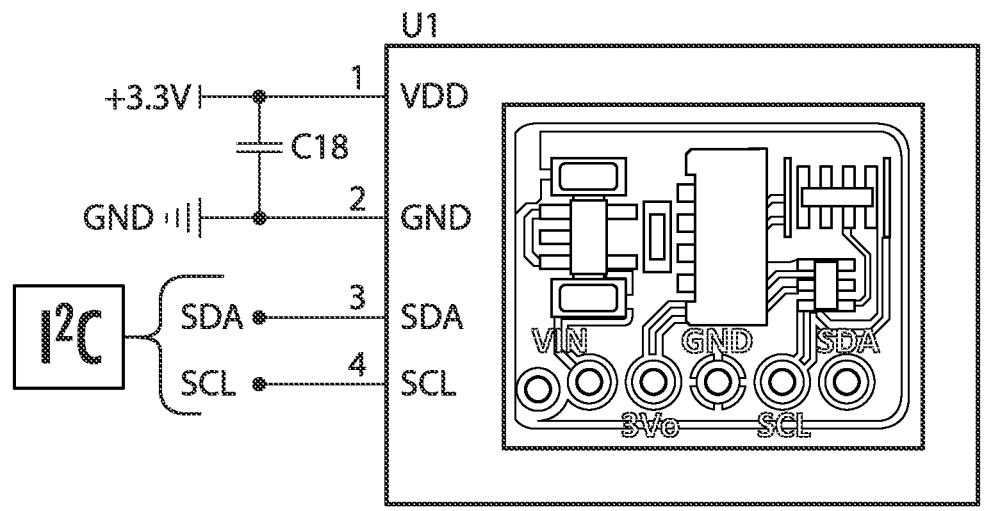
FIG. 5 is a schematic diagram of an example of an electronic illuminator's ambient light sensor chipset.

Turning now to FIG. 5, a schematic diagram of an example of an electronic illuminator's ambient light sensor chipset. There are three main types of ambient light sensors, namely, photodiodes, photonic ICs, and phototransistors. In principle they work along the same lines of converting light to voltage or current, and using the voltage or current for modes of operation. Typically, light enters the photodiode, wherein a thin layer allows photons to pass through it into a depletion region where a pair of electron holes are formed. The electric field across the depletion region causes electrons to be swept into an N layer. In some aspects, the ambient light sensor provides linear response over a wide dynamic range from 0.01 lux to 64,000 lux. The lux (symbol: 1x) is the SI derived unit of illuminance, measuring luminous flux per unit area. It is equal to one lumen per square meter. In photometry, this is used as a measure of the intensity, as perceived by the human eye, of light that hits or passes through a surface.

Illuminance is analogous to the radiometric unit watt per square meter, but with the power at each wavelength weighted according to the luminosity function, a standardized model of human visual brightness perception. Illuminance is a measure of how much luminous flux is spread over a given area. One can think of luminous flux (measured in lumens) as a measure of the total "amount" of visible light present, and the illuminance as a measure of the intensity of illumination on a surface. A given amount of light will illuminate a surface more dimly if it is spread over a larger area, so illuminance is inversely proportional to area when the luminous flux is held constant.

The illuminance provided by a light source on a surface perpendicular to the direction to the source is a measure of the strength of that source as perceived from that location. Like all photometric units, the lux has a corresponding "radiometric" unit. The difference between any photometric unit and its corresponding radiometric unit is that radiometric units are based on physical power, with all wavelengths being weighted equally, while photometric units take into account the fact that the human eye's image-forming visual system is more sensitive to some wavelengths than others, and accordingly every wavelength is given a different weight. The weighting factor is known as the luminosity function.

The lux is one lumen per square meter (lm/m2), and the corresponding radiometric unit, which measures irradiance, is the watt per square meter (W/m2). There is no single conversion factor between lux and W/m2. There exists a different conversion factor for every wavelength, and it is not possible to make a conversion unless one knows the spectral composition of the light. The peak of the luminosity function is at 555 nm (green); the eye's image-forming visual system is more sensitive to light of this wavelength than any other. For monochromatic light of this wavelength, the amount of illuminance for a given amount of irradiance is maximum: 683.002 lux per 1 W/m2; the irradiance needed to make 1 lux at this wavelength is about 1.464 mW/m2. Other wavelengths of visible light produce fewer lux per watt-per-meter-squared. The luminosity function falls to zero for wavelengths outside the visible spectrum.

For a light source with mixed wavelengths, the number of lumens per watt can be calculated by means of the luminosity function. In order to appear reasonably "white", a light source cannot consist solely of the green light to which the eye's image-forming visual photoreceptors are most sensitive, but must include a generous mixture of red and blue wavelengths, to which they are much less sensitive.

This means that white (or whitish) light sources produce far fewer lumens per watt than the theoretical maximum of 683.002 lm/W. The ratio between the actual number of lumens per watt and the theoretical maximum is expressed as a percentage known as the luminous efficiency. For example, a typical incandescent light bulb has a luminous efficiency of only about 2%. In reality, individual eyes vary slightly in their luminosity functions. However, photometric units are precisely defined and precisely measurable. They are based on an agreed-upon standard luminosity function based on measurements of the spectral characteristics of image-forming visual photoreception in many individual human eyes.

In the example of FIG. 5, an ambient light sensor, configured as an ambient light sensor subsystem is integrated into the rigid-flex printed circuit board. By integrating the ambient light sensor, the electronic illuminator possesses the ability to visualize or detect the connection of the fiber feed by determining environmental lux, and the change in lux once the fiber is configured. An increase of lux within the housing, without an increase in the lux externally to the electronic illuminator may single that the onboard LED is active, but transmission through the fiber optic line is not occurring. Similarly, with ambient lux increased, from powering on of the LED drivers, it may signal that the electronic illuminator is operating as intended.

In other aspects, there exists a translucent ring at the proximal location of the illuminator to detect the ambient light difference from that of the LED's of the electronic illuminator. In one aspect, the ambient light sensor is placed on a flexible region of a RF-PCB in a location that is shaded from luminance of the fiber source. If the ambient light sensor detects ambient light with no fiber attached it can switch the microcontroller into low power mode. The ambient light sensor, in other aspects, assists with power control and sleep wake. In other aspects, the ambient light sensor detects errors within the LED or within the electronic illuminator. The ambient light sensor, in additional embodiments is equipped to detect occlusion of the signal of the electronic illuminator and to alert or otherwise inform users of an issue with the electronic illumination system.

Referring now to FIG. 6, an illustration of an example of an electronic illuminator in cross section, disclosing the ambient light sensor configuration within the electronic illuminator. In the example, the ambient light sensor is configured in a region shaded from the LED 604 of the electronic illuminator. The ambient light sensor 614 is directed to receive lux or light from the environment through the translucent ring 616. In additional embodiments, the translucent ring 616 may have a filter to shade certain lux ranges so as to enable optimal performance. If the ambient light sensor 614 detects ambient light with no fiber attached it can switch the microcontroller or MCU into low power mode. The ambient light sensor 614, in other aspects, assists with power control and sleep wake. In other aspects, the ambient light sensor detects errors within the LED or within the electronic illuminator. The ambient light sensor, in additional embodiments is equipped to detect occlusion of the signal of the electronic illuminator and to alert or otherwise inform users of an issue with the electronic illumination system.

Continuing, in FIG. 6, the R/G/B sensor 612 forming the cap color detection assembly is facing towards the receiving orifice of the fiber 618 and fiber funnel cap 620. The R/G/B sensor being equipped to read the outer surface of the inserted portion of the fiber funnel cap 620. Further, the R/G/B sensor is able to detect the color of the fiber funnel cap 620 for instructing the MCU to power LED drivers for a specific color or for other computational routines.

Referring now to FIG. 7, an illustration of an example of an electronic illuminator's Rigid-Flex PCB 700, wherein the flex portion is disclosed with the ambient light sensor 702 and the cap color detection assembly configured with an R/G/B sensor 704. The cap color detection assembly having the capability to read the cap color of a fiber side cap, to program the LED power drivers to illuminate a specific range of LED light to match the fiber side cap. In one aspect, the RGB sensor may be color light sensing with an IR blocking filter and with high sensitivity. Example manufacturers include Misumi™, Excelitas™, ams™, and include low power options with high sensitivity.

Examples of Benefits and Features for an R/G/B Sensor are disclosed in the table below:

| R/G/B Sensor | |
| --- | --- |
| Benefits | Features |
| Enables accurate color and light sensing measurements under varying lighting conditions by minimizing IR and UV spectral component effects | Red, Green, Blue (RGB), and Clear Light Sensing with IR blocking filter Programmable analog gain and integration time 3,800,000:1 dynamic range Very high sensitivity |
| Programmable interrupt pin enables level-style interrupts when pre-set values are exceeded, thus reducing companion microprocessor overhead | Maskable interrupt Programmable upper and lower thresholds with persistence filter |
| Enabling a low-power wait-state between RGBC measurements to reduce average power consumption | Power management Low power - 2.5 µA sleep state 65 µA wait state with programmable wait state time from 2.4 ms to >7 seconds |
| Digital interfaces are less susceptible to noise | I²C fast mode compatible interface Data rates up to 400 kbit/s Input voltage levels compatible with VDD or 1.8 VBUS |

In one aspect, an R/G/B sensor, as part of the cap color detection assembly is configured to read a multiple band code, wherein the bands may be coded or preprogrammed within the MCU to illuminate at a specific spectrum, such as to produce a specific color of light. The multiple band code may be transcribed as rings on a fiber side cap or along the fiber line, that when engaged with the electronic illuminator allows reading of the multiple band code and transmission from the cap color detection assembly to an MCU for signaling or communicating to the LED power drivers.

Figure 8:
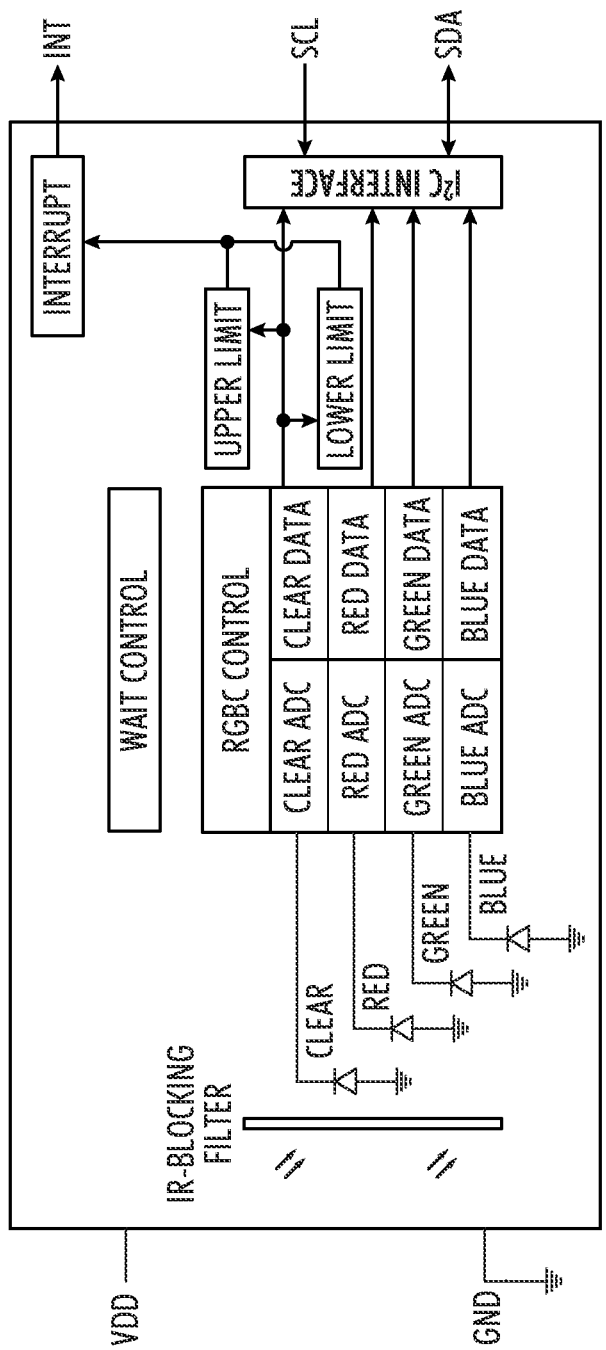
FIG. 8 is a block diagram of an example of an electronic illuminator's cap color detection assembly.

Referring now to FIG. 8, a block diagram of an example of an electronic illuminator's R/G/B sensor forming a cap color detection assembly. In the block diagram, the R/G/B control stack shows the architecture of the integrated circuit. Further, the R/G/B sensor is in interface communication with an MCU on a RF-PCB. The configuration is one of many, other examples may include additional components or configurations. For example, a multiple band code reader may contain additional elements.

In one aspect, a cap color assembly utilizes an R/G/B sensor to identify the cap color, wherein once acquired, communicates with an MCU which in turn instructed LED power drivers to illuminate for the specific color. In other aspects, a cap color detection assembly may be coded to specific instructions, such as to illuminate with a pattern, or to indicate expected luminosity outside of the ambient light sensor, to play an audio signal, or other cognitive aspect such as identifying with medical fluid treatment. In one aspect, a red cap or red band pattern may be programmed for blood products, or blood infusion. Whereas a green cap or green band pattern may be programmed for nutrients, and blue for saline, these are but a few possibilities with the systems and methods disclosed herein.

Figure 9:
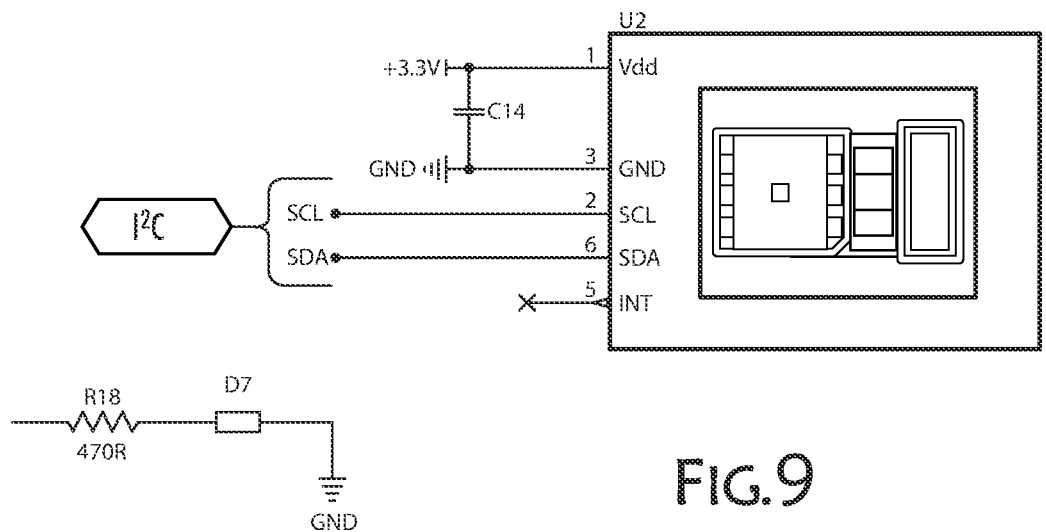
FIG. 9 is a schematic diagram of an example of an electronic illuminator's R/G/B sensor forming a part of the cap color detection assembly.

Referring now to FIG. 9, a schematic diagram of an example of an electronic illuminator's R/G/B sensor forming a part of the cap color detection assembly. In the example of FIG. 9, a schematic for one embodiment of an R/G/B sensor is disclosed. The MCU on the RF-PCB in communication through the I²C interface. In one aspect the cap color detection sensor minimizes IR and UV spectral component to produce accurate color measurements. In another aspect the cap color detection detects the cap color of the fiber funnel cap on the side scattering fiber optic line. In other aspects the cap color detection assembly detects the color of the fiber funnel cap and registers the color with the microcontroller or MCU. In this example, the microcontroller determines what color the fiber funnel cap consists of and signals to the LED driver to illuminate the side scattering fiber optic line with the specific color. The cap color detection assembly is enabled to scan for accurate color under varying conditions, ranging from ICU room lighting to patient care and resting state lighting. Furthermore, the fiber funnel cap color may serve as a watermark, proprietary colors may be selected, and or techniques of encoding the fiber funnel caps with color properties for counterfeiting prevention and authentication. Furthermore, the cap color detection assembly is capable of SKU identification, identifying aspects of readable codes such as bar codes, QR codes, band codes, color codes or other patterns of identifying information. Such identification allows for authenticating and verifying medical equipment, which in turn helps reduce risk of patient harm, and allows the system to operate in normal fashion.

Figure 10:
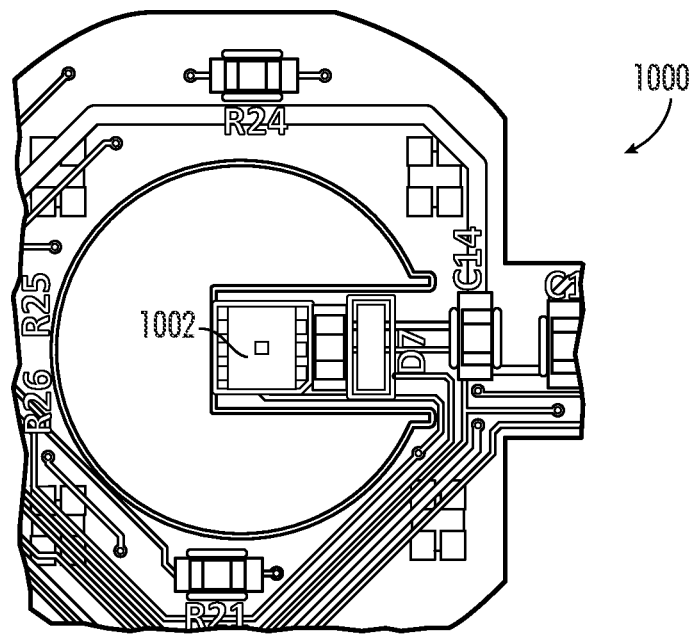
FIG. 10 is an illustration of an example of an electronic illuminator's Rigid-Flex PCB, wherein the flex portion is disclosed with the cap color detection assembly.

Referring now to FIG. 10, an illustration of an example of an electronic illuminator's Rigid-Flex PCB, wherein the flex portion is disclosed with the cap color detection assembly 1000. In one aspect the R/G/B sensor 1002 has an IR filter and white LED module. An example of an R/G/B sensor is the TCS34725, manufactured by TAOS™ (Texas Advanced Optoelectronic Solutions). In one aspect the R/G/B sensor 1002 returns and processes analog to digital values for a sensed object, such as a cap or band pattern. Further, in some aspects, the R/G/B sensor 1002 of the cap color detection assembly 1000 also allows for ambient light sensing for functions such as power savings, in use, security, and authentication. In one aspect the R/G/B sensor 1002 contains an 3×4 photodiode array and four analog to digital converters that integrate the photodiode, data registers, a state machine, and an I²C interface.

In additional aspects a watermark, or color array, for a series of color bands may be used for security and authentication. In one aspect a series of banded color codes is placed and read by the cap color detection assembly within the electronic illuminator. If the color code is a match the electronic illuminator functions, if the color code is not a match the electronic illuminator provides notification. Notification can consist of a signal or transmission, or other notification that the fiber is either not genuine, or is inserted incorrectly, or there is a failure within the system. Additionally, in another aspect, the color bands or watermark may also provide input to the electronic illuminator regarding the LED transmission color to illuminate the fiber line with.

Figure 11:
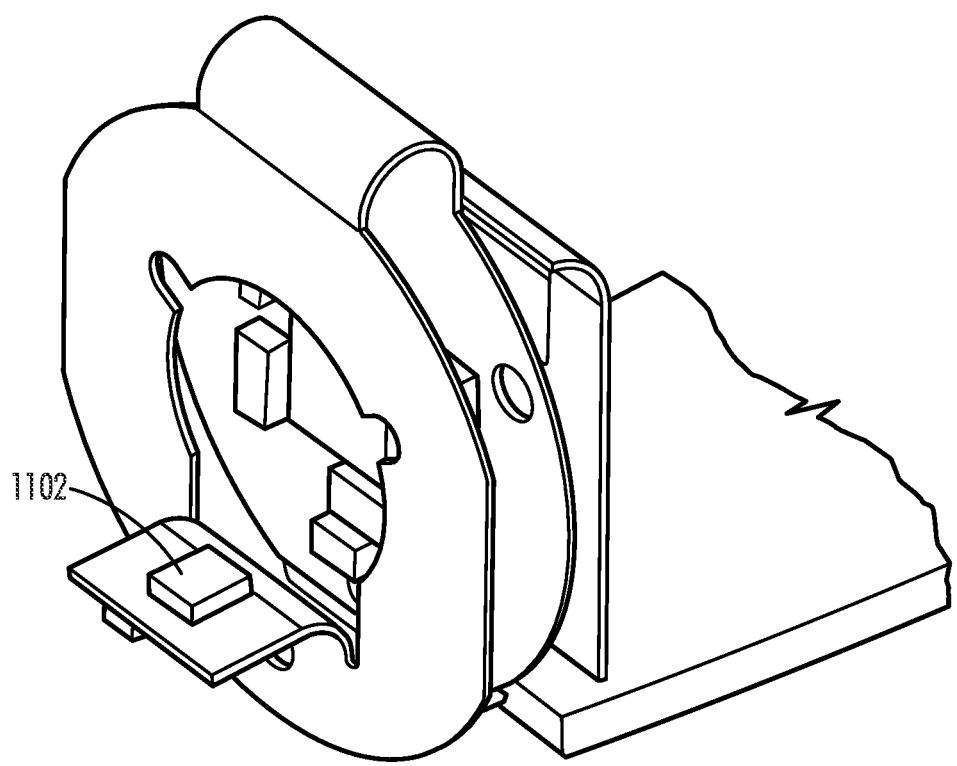
FIG. 11 is an illustration of an example of an electronic illuminator, disclosing the cap color detection assembly configuration within the electronic illuminator.

Referring now to FIG. 11, an illustration of an example of an electronic illuminator, disclosing the cap color detection assembly configuration within the electronic illuminator. In the example view the fiber funnel cap is disclosed wherein it is configured with the electronic illuminator. The R/G/B sensor 1102 of the cap color detection assembly is configured to interface with the fiber funnel cap of the side scattering fiber optic line. Further, the position of the R/G/B sensor 1102 also accounts for reading of a unique band code or code on the cap side or fiber funnel cap that codes for a specific light, or for authentication, or additional features as programmed within the system. In one aspect, the multiple band code identifies red and the power driver of a red LED is turned on.

Referring now to FIG. 12, an illustration of an example translucent cap 1200 and magnet array 1202 for an electronic illuminator, the configuration provides aspects of the fiber detection assembly. The cap may be translucent and work in coordination with the optical sensor disclosed above, for sensing environmental light and light leakage from the side scattering fiber optic line. The translucent cap 1200 is fitted to the electronic illuminator forming a part of the housing. Disclosed within FIG. 12 is positioning for a plurality of magnets to form a magnetic field. Such field may be utilized for authentication, activation, security, and transmission of information utilizing a specific flux key or signature.

Similarly, referring to FIG. 13, an additional illustration of an example translucent cap and magnet array 1302 with a steel bar 1304 for an electronic illuminator, the configuration provides aspects of the fiber detection assembly. The steel bar 1304 provides tuning of magnetic field to allow for tuning of specific fields, allowing for more than authentication, but having different flux keys or signatures result in different effects, such as programmed to a specific color, or pattern for the LED driver. With regard to authentication, the steel bar 1304 may also be a magnetic bar and it is utilized in tuning, the electronic illuminator may also not require a steel bar 1304 and the system may operate with a three dimensional magnetic flux based on the magnet array 1302, wherein the key or signature is determined by the metallic plate on the fiber funnel cap being engaged with the electronic illuminator.

Referring now to FIG. 14, an illustration of an example fiber detection assembly, wherein the Rigid-Flex PCB 1400 is disclosed with a Hall sensor 1402. A Hall sensor also known as a Hall-effect sensor is a device that measures the magnitude of a magnetic field. A Hall sensor's output voltage is directly proportional to the magnetic field strength through it. Hall sensors are used for proximity sensing, positioning, speed detection, and current sensing applications. Frequently, a Hall sensor is combined with threshold detection, so that it acts as and is called a switch. Commonly seen in industrial applications, Hall sensors are also used in consumer equipment and medical applications; for example, some computer printers use Hall sensors to detect missing paper and open covers. They can also be used in computer keyboards, an application that requires ultra-high reliability. An example of a Hall sensor is the US1881 by Melexis™ that is based on mixed signal CMOS technology. In one aspect, the Hall sensor is equipped with high magnetic sensitivity, has an operating voltage of 3.5V up to 24V, and a low current consumption.

In one aspect, the Hall sensor 1402 on the electronic illuminator detects the presence of the fiber line through a series of magnets placed on the front cap of the electronic illuminator. In one embodiment the electronic illuminator creates a 3D magnetic flux density that is capable of sensing to +/−160 mT. In other embodiments a range exists over +/−160 mT. The Hall sensor is equipped with a programmable flux resolution to 65 uT. Therefore, enabling position detection and X-Y angular and fiber orientation and measurements. The 3d magnetic flux is also known as a magnetic flux key or signature, and such signature can be used for authentication and verification of the illuminating infusion line or the fiber line. Further, in other aspects, the Hall sensor 1402 controls the power supply and sleep wake functionality. The hall sensor 1402 is further equipped to provide energy saving aspects by controlling functionality of on/off, sleep/wake, rest state of a microcontroller. In other aspects, the Hall sensor 1402 enables device security through detection of a flux key or signature.

In the example of FIG. 14, in one aspect of the electronic illuminator a plurality of magnets for a magnetic field that can be registered by onboard sensors, such as a hall sensor, the flux may be used to verify the device is in use or other aspects such as security and authentication. In such a scenario the magnetic field is tuned to a flux key or signature so as to authentic the device. In one aspect a steel pin is utilized to adjust the flux field, in another a different material capable of disturbing magnetic force is used. In one aspect the steel pin is set to match the signature of a specific fiber funnel cap color of illuminating fiber optic line. In another aspect, the steel pin or other magnetic flux disturbing device, is positioned for specific voltage readings from the Hall sensor. In such an embodiment authenticating the various attachment fiber optic lines can be observed. Further, in additional embodiments the sleep wake function of the microcontroller may be activated by the Hall sensor, thus allowing power conservation.

Continuing with FIG. 14, in one aspect the fiber funnel cap may be a specific color that designates the color of LED light the LED power driver will illuminate within the electronic illuminator. The fiber funnel cap is located proximal to the electronic illuminator, and at the opposite end of where the fiber line terminates. The distal end of the fiber optic line may have a protective proximal cap. In one aspect, the fiber funnel cap may be equipped with a metal plate to match and verify a specific signature (flux key, flux signature) wherein the electronic illuminator's Hall sensor, as part of the fiber line detection assembly, can sense and acknowledge the signature. In some aspects, the fiber side cap, equipped with a magnetic plate is used for authentication and verification. In other aspects, the fiber side cap is utilized for providing instruction to the electronic illuminator. In additional aspects, an antenna may be placed on the proximal cap cover of the fiber line, in which the microcontroller may send a radio pulse and receive a signal, this embodiment may be tied to an optical power sensor, or the microcontroller, or both.

Figure 15:
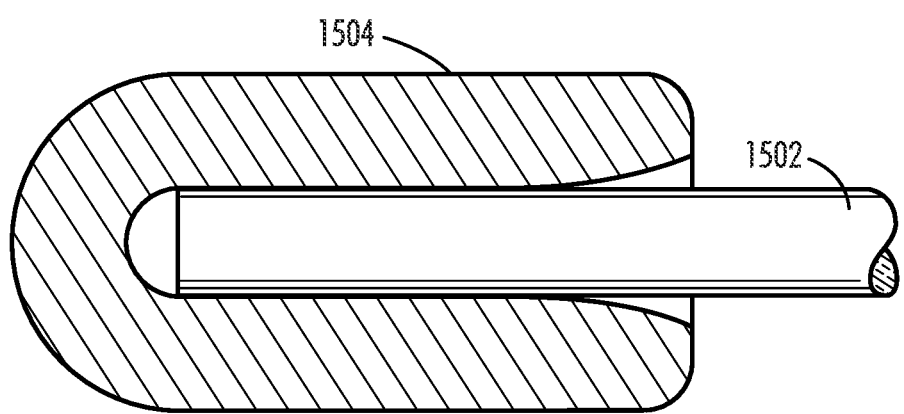
FIG. 15 is an illustration of a distal end cap on a fiber optic line also known as a side scatter or side emitting fiber optic line.

Referring now to FIG. 15, an illustration a distal end cap of a side scattering or side emitting fiber optic line. In the example the protective end cap 1504 for the side scattering fiber optic line 1502 has a polished or painted surface that is highly reflective of light. The polished or painted surface allows for reflection, similar to a mirror, wherein the programmed MCU on the PCB may initiate a sequence of flashes or pulses for authentication or verification. These pulses or flashes emanate from the LED on the electronic illuminator, travel the length of the side scattering fiber optic cable, and are reflect back from the protective end cap into the electronic illuminator where the ambient light sensor detects the pulses or flashes and interprets the signal. Additionally, a routine of pulsed light may be used for signaling the length of the fiber optic line 1502, for regulating intensity of the LED and thus controlling power drivers and saving power. If the pulsed light is not returned at a specific strength of lux it may be determined the side scattering fiber optic line is too long for usage or it may adjust power of the LED in order to broadcast along a longer fiber optic cable. This may work in coordination with the ambient light sensor, disclosed previously, to regulate power output based on the environmental light and length of the fiber optic line 1502.

Continuing, the protective end cap 1504, with a polished surface, is also made of a resilient material such as a hard plastic or metal that allows for protection of the fiber optic line 1502 so it does not fray or come into contact with patients. Additionally, the protective end cap is smooth and made to be non-abrasive and easy to clean, with no openings or otherwise which allows for prevention of bacterial growth and reusability.

Further, the protective end cap 1504 may be equipped with a one line antennae that is utilized for communicating over radio frequency, thus adding an additional layer of communication to the fiber optic line. The one line antennae acts as a passive wireless antenna and may be used for determining fiber optic line length or for verification and authentication.

Referring now to FIGS. 16A-C, disclosed are various aspects of a fiber funnel cap 1602 that is designed to engage with the electronic illuminator, through the translucent ring or other receiving assembly on the housing to the lens of the electronic illuminator for transmitting line through the side scattering or side emitting fiber optic line. The fiber funnel cap, in one aspect, is also configured with a metal plate that may be utilized for magnetically locking the cap into the electronic illuminator or for tuning with a magnetic flux. For example, the metal plate 1604 may also be used for authentication and verification in coordination with the fiber detection assembly and the onboard hall sensor by a magnetic flux key or signature. In this regard, the metal plate 1604 is characterized by a specific angle vector relative to the onboard magnet assembly of the electronic illuminator, thus creating a magnetic flux signature or key.

Continuing, the fiber funnel cap 1602 may come in a variety of colors and the color is detected by the cap color detection assembly, wherein the MCU may power an LED driver to the specific cap color. Further, the fiber funnel cap 1602 may be equipped with bands, such as a multiple band code, or a SKU, or QR code, that allows for the R/G/B sensor of the cap color detection assembly to read the bands or code and transmit to the MCU a signal for the color to illuminate by the LED power driver. Therefore, the fiber optic cable, including the fiber funnel cap may be "programmed" from manufacture to illuminate a specific LED driver within the electronic illuminator. The system therefore reduces cognitive load on practitioners as the fiber funnel caps are coded with the matching color, reducing overhead and allowing design to provide function.

Figure 17:
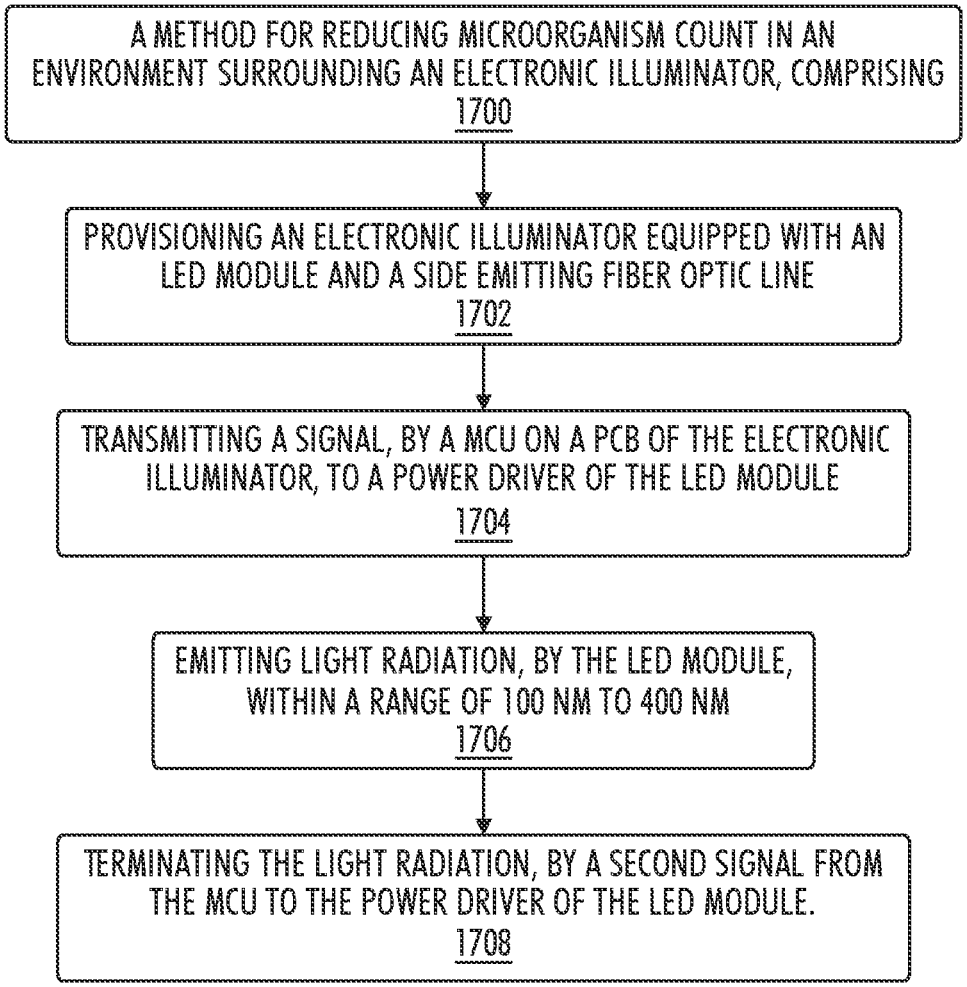
FIG. 17 is a flow chart of an example method for reducing microbial load in an environment around the electronic illuminator and side scattering fiber optic line.

Now referring to FIG. 17, a flow chart of an example method for reducing microbial load in an environment around the electronic illuminator and side scattering fiber optic line. In the example, a method for reducing microorganism count in an environment surrounding an electronic illuminator 1700 is disclosed. In the example, an electronic illuminator is provisioned 1702, wherein the electronic illuminator is equipped with an LED module, such as an LED power driver and R/G/B, white LED's that are capable of emitting within a range of 100 nanometers ('nm') to 400 nanometers. This range is variable all the way to 10 nanometers. Additionally, the LED assembly is capable of emitting in the visible spectrum from 380 to 750 nanometers for illuminating the side emitting fiber optic cable.

Continuing, the electronic illuminator, being equipped with an onboard PCB and microcontroller, also known as an MCU, transmits a signal to a power driver to power the LED within a range of 100 nm to 400 nm, for a duration that is configurable based on environmental needs or location. In other aspects, a special UVC LED module may be equipped for broadcasting from the 10 nm to 80 nm range. In one example, spectrum near the 400 nm range may be utilized when a patient is nearby or when the environment is not clear of practitioners and patients. Whereas, strong, UVC range spectrum may be utilized or a longer duration of UVA when patients and practitioners are not in the surrounding environment. Further, the "cleaning" process may begin when the ambient light sensor detects no external environmental light, thus the electronic illuminator may be in storage or away from use, wherein it will automatically turn on a cleaning routine to prepare for the next use or to otherwise aid in reducing microorganism load within an environment.

Continuing with FIG. 17, the electronic illuminator's LED assembly emits light radiation, thereby performing an operation designed to reduce microorganism load. 1706. Lastly, when the sequence of UV radiation completes, the MCU on the electronic illuminator signals to the LED power drivers to turn off 1708. Tis process may be automated based on environmental light, Bluetooth or other radio frequency initiating the process, a set timer, or an algorithm based on motion sensing of the electronic illuminator. For example, the provisioned electronic illuminator may be equipped with a gyroscope, wherein detection of movement has ceased for a period of time, then the cleaning sequence of UV radiation may begin.

Continuing, the LED power drivers may emit light for a set duration such as for at least 30 seconds. Or it may be equipped to emit light for a specific scenario, for instance, in an emergency room the duration of cleaning with UVA may be for fifteen minutes when the environment is not occupied. The duration may also be altered by whether the device is quipped to battery power or whether it is plugged directly to a wall socket or on wireless charging. In one aspect a near white LED light is activated within the UVA spectrum, wherein the illumination may be controlled by the onboard cap color detection assembly in coordination with the ambient light sensor. In that regard, the cleaning routine may be performed when parameters such as reduced or no ambient light, also referred to as environmental light, exists, along with a missing or not detected fiber funnel cap.

Additionally, the LED assembly may be equipped for intense pulsed light ('IPL') to deliver broad spectrum pulsed light. This light is generally within the visible range of 400 to 1200 nm. The cap of the electronic illuminator or lens may be equipped with various cutoff filters for specific filtering of wavelengths. In one aspect the IPL may pulse at a duration between 20-50 ms, in other aspects the pulse duration may be longer. Further, the IPL pulse frequency may be between 3 and 15 Hz, but high frequencies are also applicable.

The table below is a sampling of UV dosages and log reduction of selected microorganisms.

|  | Dosage (μm s/cm$^2$) | Log$_{10}$ |
|---|---|---|
| Pathogen (Bacteria) | | |
| *Escherichia coli* | 3,000 | 3.5 |
| *Salmonella typhi* | 2,500 | <2 |
| *Pseudomnas aeruginosa* | 5,500 | 5.5 |
| *Salmonella enteritis* | 4,000 | 5 |
| *Legionella pneumophila* | 380 | 1.9 |
| Pathogen (Virus) | | |
| Poliovirus 1 | 5,000 | 5 |
| Hepatitis A | 3,700 | 5.5 |
| Rotavirus SA 11 | 8,000 | 9.1 |
| Pathogen (Protozoa) | | |
| *Giardia muris* | 82,000 | <1.9 |

Further, UVC is known to achieve a lethal dose of 99.99 at 108.714 mJ/cm$^2$ with an exposure time of less than 50 seconds. The disclosure herein is capable of configuring an LED UVC module that is configurable for the desired lethal dose, provided power requirements and thermals are satisfied. Such adaptations to the current configuration include increasing the power driver, increasing thermal heat sink size and position, and accommodating larger LED modules. Furthermore, embodiments herein may be further configured to a medical infusion pump, wherein the larger size and dimensionality will provide for increased LED size and performance as it relates to UV radiation output for reducing microorganism load.

IV. Embodiments

Certain implementations of systems and methods consistent with the present disclosure are provided as follows:

Implementation 1. A system for reducing microorganism load in an environment surrounding an electronic illuminator, comprising: an electronic illuminator, comprising: an LED module; a power driver, for driving power to the LED module; a housing, a PCB configured with an MCU; a side emitting fiber optic line, comprising: a fiber funnel cap; and a protective end cap.

Implementation 2. The system of implementation 1, wherein the LED module is capable of transmitting light radiation at a frequency of 315 nm to 400 nm.

Implementation 3. The system of implementation 1, wherein the LED module is capable of transmitting light radiation at a frequency of 280 nm to 315 nm.

Implementation 4. The system of implementation 1, wherein the LED module is capable of transmitting light radiation at a frequency of 100 nm to 280 nm.

Implementation 5. The system of implementation 1, wherein the LED module is comprised of an R/G/B LED components.

Implementation 6. The system of implementation 1, wherein the LED module is comprised of UVC LED components.

Implementation 7. The system of implementation 1, wherein the protective end cap comprises a reflective surface for reflecting light radiation back towards the electronic illuminator.

Implementation 8. The system of implementation 1, wherein the fiber funnel cap is configured with a readable code that instructs light radiation frequency and duration.

Implementation 9. A method for reducing microorganism count in an environment surrounding an electronic illuminator, comprising: provisioning an electronic illuminator equipped with an LED module and a side emitting fiber optic line; transmitting a signal, by a MCU on a PCB of the electronic illuminator, to a power driver of the LED module; emitting light radiation, by the LED module, within a range of 100 nm to 400 nm; and terminating the light radiation, by a second signal from the MCU to the power driver of the LED module.

Implementation 10. The method of implementation 9, further comprising emitting light radiation from a UVC LED module.

Implementation 11. The method of implementation 9, further comprising reducing microorganism count.

Implementation 12. The method of implementation 9, wherein provisioning an electronic illuminator equipped with an LED module and a side emitting fiber optic line, further provisions a medical fluid infusion line.

Implementation 13. The method of implementation 9, wherein emitting light radiation is for a duration of at least 30 seconds.

Implementation 14. The method of implementation 9, further comprising emitting IPL from the LED module.

Implementation 15. The method of implementation 14, wherein the emitting of IPL, further comprises a pulse duration between 20-50 ms.

Implementation 16. The method of implementation 14, wherein the emitting of IPL, further comprises a pulse frequency within 3-15 Hz.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system for reducing microorganism load in an environment surrounding an electronic illuminator, comprising:
    an electronic illuminator, comprising:
        a light emitting diode (LED) module;
        a power driver, for driving power to the LED module;
        a housing; and
        a printed circuit board (PCB) configured with a microcontroller unit (MCU);
    a side emitting fiber optic line for attaching to the electronic illuminator to receive light from the LED module and scatter the light outside of a patient and in the environment, comprising:
        a fiber funnel cap for the attaching to the electronic illuminator;
        a side emitting fiber attached to the fiber funnel cap at a proximal end; and
        a protective end cap attached to the side emitting fiber at a distal end.

2. The system of claim 1, wherein the LED module is capable of transmitting light radiation at a frequency of 315 nm to 400 nm.

3. The system of claim 1, wherein the LED module is capable of transmitting light radiation at a frequency of 280 nm to 315 nm.

4. The system of claim 1, wherein the LED module is capable of transmitting light radiation at a frequency of 100 nm to 280 nm.

5. The system of claim 1, wherein the LED module is comprised of an R/G/B LED components.

6. The system of claim 1, wherein the LED module is comprised of UVC LED components.

7. The system of claim 1, wherein the protective end cap comprises a reflective surface for reflecting light radiation back towards the electronic illuminator.

8. The system of claim 1, wherein the fiber funnel cap is configured with a readable code that instructs light radiation frequency and duration.

9. A method for reducing microorganism count in an environment surrounding an electronic illuminator, comprising:
    provisioning an electronic illuminator, comprising:
        a light emitting diode (LED) module;
        a power driver, for driving power to the LED module;
        a housing; and
        a printed circuit board (PCB) configured with a microcontroller unit (MCU);
    provisioning a side emitting fiber optic line for attaching to the electronic illuminator to receive light from the LED module and scatter the light outside of a patient and in the environment, comprising:
        a fiber funnel cap for the attaching to the electronic illuminator;
        a side emitting fiber attached to the fiber funnel cap at a proximal end; and
        a protective end cap attached to the side emitting fiber at a distal end;
    transmitting a signal, by the MCU on the PCB of the electronic illuminator, to the power driver of the LED module;
    emitting light radiation, by the LED module, within a range of 100 nm to 400 nm; and
    terminating the light radiation, by a second signal from the MCU to the power driver of the LED module.

10. The method of claim 9, further comprising emitting light radiation from a UVC LED module.

11. The method of claim 9, further comprising reducing microorganism count.

12. The method of claim 9, wherein provisioning an electronic illuminator equipped with an LED module and a side emitting fiber optic line, further provisions a medical fluid infusion line.

13. The method of claim 9, wherein emitting light radiation is for a duration of at least 30 seconds.

14. The method of claim 9, further comprising emitting intense pulsed light (IPL) from the LED module.

15. The method of claim 14, wherein the emitting of IPL, further comprises a pulse duration between 20-50 ms.

16. The method of claim 14, wherein the emitting of IPL, further comprises a pulse frequency within 3-15 Hz.

* * * * *